United States Patent [19]

Parry et al.

[11] 4,157,390
[45] Jun. 5, 1979

[54] PROCESS FOR VACCINE PREPARATION

[75] Inventors: Stephen H. Parry; Philip Porter, both of Bedford, England

[73] Assignee: Internationale Octrooi Maatschappij "Octropa" B.V., Rotterdam, Netherlands

[21] Appl. No.: 927,577

[22] Filed: Jul. 24, 1978

Related U.S. Application Data

[63] Continuation of Ser. No. 794,384, May 6, 1977, which is a continuation of Ser. No. 694,613, Jun. 10, 1976, abandoned.

[30] Foreign Application Priority Data

Jun. 12, 1977 [GB] United Kingdom ............... 25221/77

[51] Int. Cl.$^2$ ............................................. A61K 39/02
[52] U.S. Cl. ................................................. 424/92
[58] Field of Search ........................................ 424/92

[56] References Cited
FOREIGN PATENT DOCUMENTS 1413799  11/1975  United Kingdom.

OTHER PUBLICATIONS

Neter et al., J. Bacteriol, 66:424–428, (1953), "The Requirement of Electrolytes for the Adsorption of *Escherichia Coil* Antigen by Red Blood Cells".

Kabat et al., Experimental Immunochemistry, 2nd Ed., (1961), C. C. Thomas, Springfield, Ill., p. 97, Agglutination, 119–124, "Adsorption of Antigens on Untreated Erythrocytes-Coupling of Antigens to Erythrocytes".

Jones et al., J. Gen. Microbiol. 84(1): 135–144, Jan.-Feb. 1974, "The Association of K88 Antigen With Haemagglutinating Activity in Porcine Strains of *E. Coli*".

Jones et al., Am. Jl. Clin. Nutr., (1974), 27(12):1441–1449, "Contribution of the K88 Antigen of *Escherichia Coli* to Enteropathogenicity; Protection Against Disease by Neutralizing the Adhesive Properties of K88 Antigen".

*Primary Examiner*—Shep K. Rose
*Attorney, Agent, or Firm*—Barry Kramer

[57] ABSTRACT

A vaccine comprising an antigen selectively adsorbed onto erythrocytes possessing their natural surface characteristics. When the antigen is the K88a,b/adhesion factor of *E. coli* and the erythrocytes are chicken erythrocytes, the vaccine is especially suitable for reducing the incidence of neonatal diarrhoea in pigs if it is administered parenterally to a sow about three weeks prior to parturition.

3 Claims, No Drawings

PROCESS FOR VACCINE PREPARATION

This is a continuation, of application Ser. No. 794,384, filed May 6, 1977 which is a continuation of application Ser. No. 694,613, filed June 10, 1976, now abandoned.

This invention relates to antigenic compositions.

The invention provides an antigenic composition comprising an antigen, in particular an enteropathogenic bacterial adhesion factor, selectively adsorbed onto unmodified erythrocytes (red blood cells), and arises from our discovery that certain unmodified erythocytes possess selective receptor sites on their surfaces and thereby are able to form complexes with particular proteins. By "unmodified erythrocytes" we means erythrocytes that possess their natural surface characteristics, as distinct from modified erythrocytes, for example erythrocytes whose surfaces have been chemically modified by contact with materials such as formaldehyde, tannic acid or glutaraldehyde, and hence have lost their natural ability to selectively form protein complexes. For any given antigen, there may be very few types of erythrocytes—perhaps only one—that are capable of selectively adsorbing that particular antigen. For any given antigen, the appropriate erythrocytes can be found by screening possible erythrocytes types to find those that are agglutinated by an aqueous solution of the antigen, adopting a procedure such as is described later herein.

For simplicity, the invention will be described in detail in relation to the enteropathogenic strains of E. coli which are specially implicated in neonatal diarrhoea of pigs. Infection of the newborn piglet with these strains can lead rapidly to dehydration and death of the piglet, and thus represents a serious problem in the production of pigs for food. Among the enterotoxin-producing strains most frequently encountered in neonatal diarrhoea are the following:

International Serotype Classification

08:K87 (B), K88a,b (L)
08:K87 (B), K88a,c (L)
015a,c:K 'E65', K88a,c (L)
0138:K81 (B), K88a,c (L)
0141:K85a,b (B), K88a,b (L)
0147:K89 (B), K88a,c (L)
0149:K91 (B), K88a,c (L)
0157:K 'V17', K88a,c (L)

In neonatal diarrhoea of the pig, the anterior small intestine is colonised by one or more of such strains, and it has been postulated that their resistance to removal from the small intestine by peristalsis is due to adhesive substances present on the surface of the bacterium. Furthermore, it has been noted that all these strains synthesise one or other of two closely related protein surface antigens designated K88a,b and K88a,c, which are substantially insoluble between pH 3.5 and 5.5, are of high molecular weight (sedimentation coefficient about 35S), and are heat-labile, being denatured when heated above 70° C. It has been suggested that it is these substances that are responsible for the gut-adhesive properties of the enteropathogenic strains of E. coli.

There are in the literature various references to the experimental administration of vaccines (ie antigen compositions) containing K88 antigen to pregnant sows in order that additional protective antibodies might be generated in the sow's circulatory immune system and, on the sow's farrowing, might pass to the colostrum (first milk) and so be made available at the site of E. coli colonisation in the gut of the suckling piglet. However, it is accepted (see J. M. Rutter "Escherichia coli infections in piglets: Pathogenesis, virulence and vaccination" in The Veterinary Record, Feb. 22, 1975, 96, 171–175) that variable results have been obtained with such vaccines: experiments with them sometimes produced positive results, and sometimes did not.

The present invention provides improved antigenic compositions for administration to pregnant sows, and arises from our discoveries that the K88a,b/adhesion factor is strongly adsorbed from aqueous media onto certain unmodified erythrocytes (red blood cells), particularly those of the chicken; that the complex thus produced is strongly immunogenic; and that the antibodies produced on parenteral administration of the complex inhibit the adhesion in the piglet gut of all the E. coli strains specified earlier, whether the K88 antigen present on the surface of those strains is K88a,b or K88a,c.

According to one embodiment of the invention, therefore, there is provided an antigenic composition comprising unmodified erythrocytes on which is adsorbed K88a,b/adhesion factor.

Preferably, the ratio of adsorbed K88a,b/adhesion factor to the volume of erythrocytes in the composition is in the range of 125–800 units per ml; and a ratio in the range of 400–800 units per ml is particularly preferred. Adhesion factor in excess of the ratio 800 units per ml may be present in the composition, but the excess is for the most part not adsorbed on the erythrocytes and is immunogenically not utilised so efficiently as the adsorbed material. The units referred to (haemogglutination units) are measured by a procedure adapted from one that is conventional in immunology, and is illustrated in Example 1 later in this specification.

The antigenic composition may be a simple aqueous one, or may contain a phase of adjuvant oil, such as mineral oil or arachis oil, whose presence enables an enhanced antibody response (enhanced by comparison with that from the simple aqueous composition) to be obtained on administration by injection. In preferred form, the composition is a multiple oil-water emulsion, of the kind generally disclosed in British Patent Specification No. 1,080,994. In this form, the continuous phase is an aqueous one (such as sterile water, physiological saline or phosphate buffer), and the antigenic material (in our case the K88a,b/adhesion factor-red blood cell complex) is present in a further (secondary) aqueous phase which is itself dispersed in a primary disperse phase of oil.

To prepare the antigenic composition, a cell-free aqueous solution containing the K88a,b/adhesion factor is brought into contact with unmodified erythrocytes, particularly unmodified chicken erythrocytes, under conditions such that the K88a,b/adhesion factor becomes adsorbed by the erythrocytes. The cell-free aqueous solution can itself be prepared from a K88a,b strain (conveniently the enterotoxic strains G7 or G68 type, obtainable from the Central Veterinary Laboratory, Ministry of Agriculture and Fisheries, New Haw, Weybridge, Surrey UK) Following generally the procedure described by Stirm, Orskov, Orskov and Mansa in J. Bacteriology, 93, 731–739. These procedures entail the release of K88 material from the surfaces of the bacteria into water, as by heating the live bacteria in an aqueous medium buffered to pH 6–9 to 60°–65° C. for 15 minutes or more, or by applying friction to the surfaces of the bacteria in the aqueous buffer, for example in a Waring Blendor. Bacteria are then removed, by filtration or centrifugation, from the aqueous K88 extracts thus obtained. The K88 material present in the cell-free extracts can, if desired (as for assay purposes), be purified by repeated isoelectric precipitation (pH about 5) and re-solution. On a large scale, a K88a,b strain of *E. coli* can be grown on a conventional casein hydrolysate/sucrose medium supplemented with the usual additives such as vitamins, under aeration (eg 3 litres/minute/10 liters of medium), with constant stirring, pH control (about 7) and temperature control (37° C.). The resulting culture is harvested at 24 hours, and centrifuged to sediment the bacteria. These are then suspended in 0.15 M saline at 3% of the original culture volume, and are then heated at about 60° C. to release the adhesion factor into the aqueous medium. Cell debris is removed by centrifugation, and the supernatant liquid is assayed for its content of adhesion factor, and the adhesion factor is then adsorbed onto chicken erythrocytes.

On parenteral administration of the antigenic composition to rabbits, sheep, rats, pigs and so forth in an entirely conventional manner, antisera are produced which can be administered orally to newborn piglets to combat neonatal diarrhoea. However, the compositions are best made use of by parenterally administering them to pregnant sows about 3 weeks before farrowing (that is, about 95 days after service by the boar), so that at parturition the colostrum contains an effective concentration of antibodies to the K88a,b/adhesion factor of enterotoxic *E. coli* strains.

The invention is further illustrated by the following Examples.

EXAMPLE 1 a. Preparation and isolation of K88a,b/adhesion factor

A pure culture of the *E. coli* strain G7 international serotype classification 08:K87 (B) K88a,b (L) was subcultured into nutrient broth and incubated at 37° C. overnight. Nutrient agar slopes in Roux flasks were heavily inoculated with the culture and incubated at 37° C. for 24 hours. The confluent surface growth was washed off and harvested aseptically using sterile 0.1 M phosphate buffer ($Na_2HPO_4/NaH_2PO_4$) pH 7.5, and the resulting bacterial suspension was heated to 60° C. for 30 minutes to release the K88a,b/adhesion factor from the cell surfaces. Cellular material was removed by centrifugation (3000 g; 10 minutes), and after the addition of sodium azide (0.2%) to prevent bacterial growth, the supernatant liquid was stored at 4° C. for 3 days. The impurities that had settled out were then removed by centrifugation, and dilute acetic acid was added to the continuously stirred supernate to reduce teh pH to 5. (The isoelectric point of the K88a,b/adhesion factor is between 4.5 and 5.5.) The precipitated material was allowed to stand for 24 hours at 4° C., then collected by centrifugation, and washed twice with 0.005 McIlvaine buffer ($Na_2HPO_4$/citric acid) pH 5.0. It was purified by repeated dissolution (using phosphate-buffered 0.15 M saline at pH 7.2) and precipitation (0.15 M McIlvaine buffer, pH 5.0). Finally, the precipitated material was dissolved in pH 7.2 phosphate-buffered 0.15 M saline and stored at −20° C.

b. Assay of K88a,b/adhesion factor in solution of unknown concentration

This assay can be used as a screening test to identify those unmodified erythrocytes that are capable of selectively adsorbing a given antigen. A portion (0.05 ml) of the solution (Y) to be assayed is serially diluted with phosphate-buffered saline pH 7.1 in successive depressions (wells) of a mictotitre plate to obtain a series of solutions of adhesion factor concentration $\frac{1}{2}, \frac{1}{4}, \frac{1}{8} \ldots \frac{1}{2^n}$ that of the solution Y. To each of these solutions is added 0.025 ml of a 2% thrice-washed (with phosphate-buffered saline pH 7.1) suspension of chicken erythrocytes in the same buffer. The plate is mechanically shaken and the well contents are allowed to settle. After $\frac{1}{2}$ hour the plate is inspected. Agglutination of the chicken erythrocytes occurs in the stronger solutions (those in the earlier filled wells) but not in the weaker ones, and the end-point of the titration (assessed at room temperature) is taken as that solution in which haemagglutination only just occurs. In a typical procedure, the end-point might be in the thirteenth well, and the titre of the solution Y would then be $2^{13}$ (=8192, say 8000, corresponding to 8000 haemagglutination (MA) units per ml).

EXAMPLE 2

Preparation of simple aqueous chicken erythrocyte vaccine

Following the procedure of 1b above, a solution prepared according to a was assayed and found to have a K88a,b/adhesion factor titre of 8000. From this solution, a vaccine was prepared by first diluting 1 ml of the solution to 10 ml with phosphate-buffered saline pH 7.1 (PBS) and then stirring the diluted solution (Z) for $\frac{1}{2}$ hour at 37° C. with 10 ml of thrice-washed (PBS) packed chicken erythrocytes obtained by centrifugation (1000 g; 10 minutes). This procedure led to substantial saturation of the chicken erythrocyte surfaces with the adhesion factor, ie there were at saturation 8000 MA units of adhesion factor per 10 ml of chicken red blood cells.

Sodium azide (0.2% by weight) was added to the resulting vaccine, which was stored at 4° C. until required for use.

The vaccine thus obtained is suitable administered to pregnant sows at a dose level of 2 ml. At this level is has about 10 times the antibody-generating effect of the (non-erythrocytes-containing) solution Z from which it was made.

Instead of using sodium azide as preservative as described above, the vaccine can be treated with formalin (40% aqueous formaldehyde solution), suitable in the proportion 1 volume of formalin:100–50 columes of the vaccine.

EXAMPLE 3

This Example illustrates the preparation of vaccines containing an oil adjuvant.

(i) 1 ml of the mannide mono-oleate emulsifier sold under the Trade Mark "Arlacel A" was dissolved in 9 ml of a pharmaceutical grade mineral oil. The oil solution was then added to an equal volume of the simple aqueous chicken erythrocyte vaccine obtained according to Example 2. Mixing was carried out in a homogeniser, to form a creamy water-in-oil emulsion.

(ii) 1 Volume of the water-in-oil vaccine of (i) was added to an equal volume of a 2% solution in 0.15 M saline of the polyoxyethylene sorbitan monooleate emulsifier sold under the Trade Mark "Tween 80". Mixing was carried out in a homogeniser.

The low-viscosity water-in-oil-in-water vaccine thus formed was injected intramuscularly at a dose level of 8 ml into sows 3 weeks before farrowing (ie about 95 days after service by the boar). The anti-adhesive activity thus generated was associated with three antibody classes (IgG, IgM and IgA) providing a wide spectrum of antibody activity, and is compared below with the corresponding activity in a control group of untreated pregnant sows.

|  | Anti-adhesive Activity | |
| --- | --- | --- |
|  | In serum | In colostrum |
| Vaccinated sows | 256 | 512 |
| Unvaccinated sows | 4–8 | 32 |

The anti-adhesive activity in the serum of piglets suckled by the vaccinated sows was 128 units; for the serum of piglets suckled by the untreated sows it was only 32 units. The piglets suckled by the vaccinated sows were far more resistant than those suckled by non-vaccinated sows to infection by enterotoxic K88a,b and K88a,c strains of *E. coli*.

What is claimed is:

1. A process for the preparation of a vaccine for parenteral administraion to pregnant mammals as a means for reducing the incidence of neonatal diarrhoea, in which process K88a,b/adhesion factor of an enteropathogenic strain of *E. coli* is adsorbed from a cell-free aqueous solution onto erythrocytes possessing their natural surface characteristics, the ratio of adsorbed K88a,b/adhesion factor to the volume of erythrocytes present being in the range 125 to 800 hemagglutination units per ml, and the composition so formed is rendered storable by the addition thereto of a preservative such as sodium azide or formalin.

2. A process as claimed in claim 1, wherein said erythrocytes are chicken erythrocytes.

3. An injectable vaccine prepared by a process as claimed in claim 1 or claim 2.

* * * * *

UNITED STATES PATENT AND TRADEMARK OFFICE
CERTIFICATE OF CORRECTION

PATENT NO. : 4,157,390
DATED : June 5, 1979
INVENTOR(S) : Stephen H. Parry; Philip Porter It is certified that error appears in the above-identified patent and that said Letters Patent are hereby corrected as shown below:

Under "Foreign Application Priority Data", the priority data should read as follows --June 12, 1975[GB] United Kingdom.....25221/75...

Signed and Sealed this

Twenty-seventh Day of November 1979

[SEAL]

Attest:

RUTH C. MASON
Attesting Officer

LUTRELLE F. PARKER
Acting Commissioner of Patents and Trademarks